United States Patent
Best

(10) Patent No.: US 9,217,522 B1
(45) Date of Patent: Dec. 22, 2015

(54) METHOD OF COUPLING NARROW DIAMETER TUBING TO A CPI PORT

(76) Inventor: John W. Best, State College, PA (US)

(*) Notice: Subject to any disclaimer, the term of this patent is extended or adjusted under 35 U.S.C. 154(b) by 0 days.

(21) Appl. No.: 13/490,424

(22) Filed: Jun. 6, 2012

Related U.S. Application Data

(62) Division of application No. 12/028,133, filed on Feb. 8, 2008, now abandoned.

(51) Int. Cl.
| | |
|---|---|
| *B21D 51/06* | (2006.01) |
| *B21K 1/76* | (2006.01) |
| *B23P 17/00* | (2006.01) |
| *F16L 13/12* | (2006.01) |
| *F16L 21/02* | (2006.01) |
| *F16L 19/06* | (2006.01) |
| *F16L 19/08* | (2006.01) |

(52) U.S. Cl.
CPC ...................... *F16L 13/12* (2013.01)

(58) Field of Classification Search
CPC ....... F16L 17/06; F16L 17/067; F16L 17/073; F16L 17/08
USPC ............... 29/456, 890.14; 285/339, 341–343, 285/348, 392, 357, 393
See application file for complete search history.

(56) References Cited

U.S. PATENT DOCUMENTS

| | | | | | |
|---|---|---|---|---|---|
| 3,313,553 | A | * | 4/1967 | Gastineau | 277/605 |
| 3,705,693 | A | * | 12/1972 | Franz | 239/600 |
| 3,841,177 | A | * | 10/1974 | Watterback | 81/467 |
| 3,851,899 | A | * | 12/1974 | Franz | 285/95 |
| 3,854,735 | A | * | 12/1974 | Maurer et al. | 277/638 |
| 4,511,152 | A | * | 4/1985 | Fournier | 277/612 |
| 4,690,437 | A | * | 9/1987 | Anderson, Jr. | 285/356 |
| 4,792,396 | A | * | 12/1988 | Gundelfinger | 210/198.2 |
| 4,900,180 | A | * | 2/1990 | Takikawa | 403/233 |
| 4,953,896 | A | * | 9/1990 | Usui | 285/197 |
| 5,188,730 | A | * | 2/1993 | Kronwald | 210/198.2 |
| 5,217,261 | A | * | 6/1993 | DeWitt et al. | 285/332.2 |
| 5,310,029 | A | * | 5/1994 | Kujawski | 188/352 |
| 5,582,723 | A | * | 12/1996 | Boone et al. | 210/198.2 |
| 6,193,286 | B1 | * | 2/2001 | Jones et al. | 285/354 |
| 6,209,928 | B1 | * | 4/2001 | Benett et al. | 285/124.1 |
| 6,494,500 | B1 | * | 12/2002 | Todosiev et al. | 285/342 |
| 6,575,501 | B1 | * | 6/2003 | Loy, Jr. | 285/342 |
| 6,926,313 | B1 | * | 8/2005 | Renzi | 285/353 |
| 7,484,776 | B2 | * | 2/2009 | Dallas et al. | 285/354 |
| 7,654,585 | B2 | * | 2/2010 | Dallas et al. | 285/354 |
| 7,984,932 | B2 | * | 7/2011 | McGuire | 285/354 |
| 8,371,621 | B2 | * | 2/2013 | Funke | 285/342 |
| 8,573,653 | B2 | * | 11/2013 | Gamache | 285/342 |

\* cited by examiner

*Primary Examiner* — David Bryant
*Assistant Examiner* — Jason L Vaughan
(74) *Attorney, Agent, or Firm* — John J. Elnitski, Jr.

(57) ABSTRACT

A coupling device for interconnecting external tubing to a port of a device. The coupling device includes a port stud, linking tube, collar, tube cap and stud nut. The port stud includes a tube opening from a top section to a bottom section of the port stud. The linking tube is sized to fit inside the tube opening of the port stud and attach to the external tubing. The collar is attached to an outside of the linking tube. The tube cap is threaded onto the top section of the port stud. The stud nut threads onto the bottom section of the port stud.

5 Claims, 5 Drawing Sheets

METHOD OF COUPLING NARROW DIAMETER TUBING TO A CPI PORT

This application is a Divisional application of U.S. patent application Ser. No. 12/028,133, filed on Feb. 8, 2008 and claims the benefit of and incorporates by reference U.S. Provisional Application No. 60/903,091 filed Feb. 23, 2007.

BACKGROUND

The present invention relates generally to the field liquid transport through narrow diameter tubing. More specifically, the present invention relates to the connection of narrow diameter external tubing to a port of a device.

Connection of narrow diameter external tubing to a fluid handling or analysis device is done using a port on the device. Common ports used in industry and research are known as a Chemical Process Industry (CPI) port, 10-32 CPI port or HPLC port. FIG. 1 shows a port 10 which are usually a threaded cavity into the device 12. The threaded cavity includes a threaded section 14, a conical section 16 and a bottom section 18, as shown in FIG. 1. The conical section 16 reduces the diameter of the threaded section 14 to that of the bottom section 18. The bottom section 18 is cylindrical in shape and has same diameter as the external tubing to be used in order to receive the external tubing. The bottom section 18 has a top 20 and a bottom 22. The top 20 of the bottom section 18 is the entrance to the bottom section 18. The bottom 22 of the bottom section 18 includes an opening 26 to the device 12 and a shoulder 24 about the opening 26. The purpose of the shoulder 24 at the bottom 22 of the bottom section 18 provides an interface between the end of the external tubing and the port. Current coupling devices to connect the external tubing to the port use a threaded member which drives a cone shaped ferrule into the conical section 16 of the port to provide clamping and sealing forces about the external tubing, typical of a compression type fitting. There are coupling devices which combine the threaded member and the cone shaped ferrule into single unit.

The current coupling devices are limited with regard to the maximum operating pressure which can be attained using the coupling device. Additionally, current coupling devices are limited with regard to eliminating parasitic effect referred to as 'dead volume' of a connection. Dead volume refers to any deviation from a cylindrical fluid path from the external tubing into the port. Dead volume occurs when the end of the external tubing to be connected to the port is not secured completely within the port. The effect of dead volume can also be present when the external tubing is deformed due to over tightening of compression fittings or improper cutting of the end of the external tubing. The current coupling devices are limited by the ability of the coned ferrule to hold the external tubing by means of friction applied by compression of the coned ferrule within the port. Even when the coupling device is properly installed using carefully prepared tubing, a negative drawback of the port design itself is that the design allows radial migration of fluids at the interface between the end of the external tubing, and the shoulder 24 of the bottom 22 of the bottom section 18 of the port.

Another aspect when using current coupling devices is the practice of using external tubing of smaller diameter than the bottom section 18 of the port. The bottom section 18 of the port is usually about one sixteenth of an inch in diameter. External tubing of one thirty-second inch diameter is commonly used with special ferrules, whereby a cylindrical section and a cone shaped section are combined end-to-end in a unified compression fitting and diameter adaptor. The cylindrical section forms a sleeve, which adapts the diameter of the external tubing to the diameter of the port. A shortcoming of this approach is the cone shaped section compresses, while the cylindrical shaped adaptor does not. This causes a void volume about the perimeter of the external tubing and within the perimeter of the cylindrical shaped section of the special ferrule. Furthermore, this type of ferrule is supplied with a fixed length cylindrical section, hence it is unable to adapt to ports with a deeper than average bottom section 18.

A final aspect of current coupling devices lies in the mechanism of failure. When pressures of fluids which are being transported through the port manifest themselves, a component of the pressure exerts a longitudinal force along the axis of the external tubing being clamped by the compression ferrule. The longitudinal force is countered solely by frictional force about the inside of the ferrule, where the ferrule contacts the external tubing. As fluids within the external tubing and volumes are pressurized and de-pressurized, a phenomenon know as 'creep' can occur. Creep causes an increasing dead volume to form between the end of the external tubing and the bottom section the port. Eventually, the external tubing will be pushed away from the bottom section and through the cone shaped ferrule, causing it to leak severely. This is commonly referred to as 'tubing blow-out'.

It is an object of the present invention to provide a coupling between narrow diameter tubing and a port of a fluid handling device in such a way as to allow high pressure levels to be attained without fluid leakage.

It is an object of the present invention to eliminate dead volume at the interface between narrow diameter tubing and the interior of a port.

SUMMARY OF THE INVENTION

A coupling device for interconnecting external tubing to a port of a device. The coupling device includes a port stud, linking tube, collar, tube cap and stud nut. The port stud includes a tube opening from a top section to a bottom section of the port stud. The linking tube is sized to fit inside the tube opening of the port stud and attach to the external tubing. The collar is attached to an outside of the linking tube. The tube cap is threaded onto the top section of the port stud. The stud nut threads onto the bottom section of the port stud.

DETAILED DESCRIPTION

Figure 1:
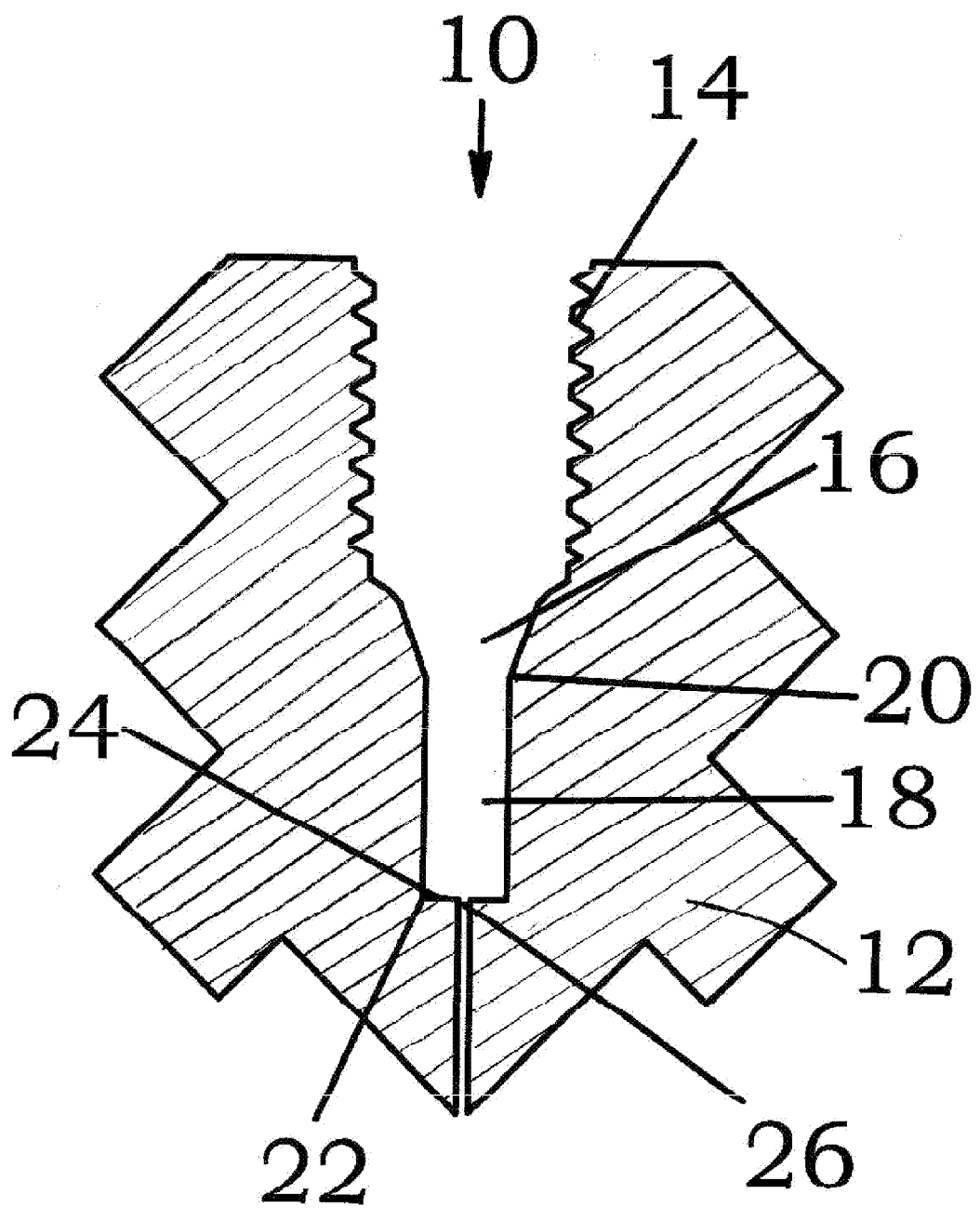
FIG. 1 is a cutaway view of a port used with a coupling device according to the present invention.
Figure 2:
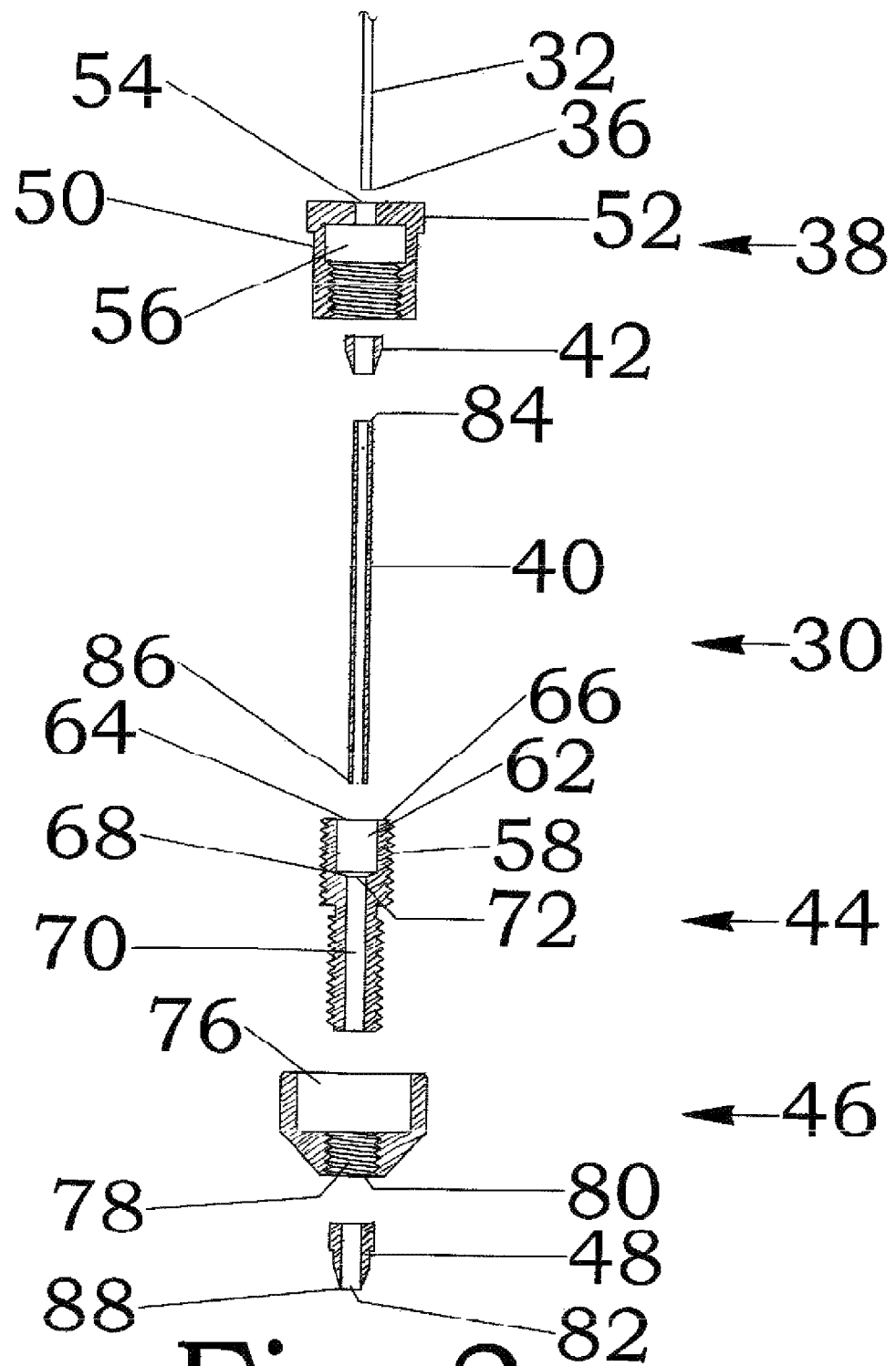
FIG. 2 is an exploded view of a coupling device according to the present invention.
Figure 3:
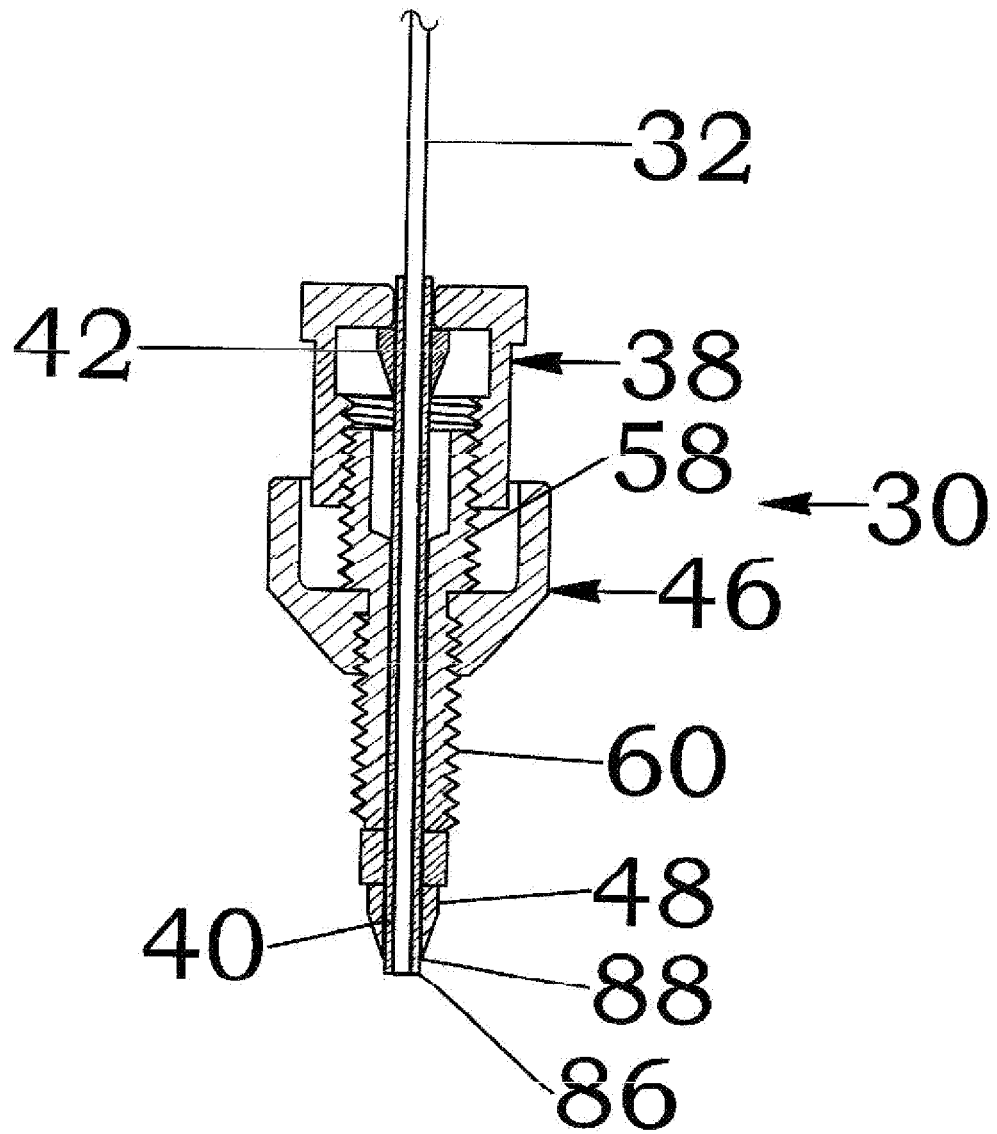
FIG. 3 is a cutaway view of an assembled coupling device according to the present invention.

The present invention is a coupling device 30 of FIG. 2 and method of use to secure a connection between external tubing 32 of FIG. 2 and a port 10 of a device 12 shown in FIG. 1. The coupling device 30 allows fluid to pass at high pressure without leaking and with minimum parasitic volume loss at the interface between the end 36 of the external tubing 32 and the port 10. The present invention may be used at one end or both ends of the external tubing 32. The coupling device includes a tube cap 38, linking tube 40, linking tube ferrule 42, port stud 44, stud nut 46 and port ferrule 48 for use with the external tubing 32 to be connected to a port 10, as shown in FIGS. 2-3.

The tube cap 38 includes a main body 50 and turn top 52. The turn top 52 is a raised surface which acts a turning surface to be gripped by the user. There is an opening 54 in the turn top 52 which leads to an open cavity 56 in the main body 50. The lower portion of the open cavity 56 of the main body 50 is threaded. The linking tube ferrule 42 is slightly larger than the opening 54 of the turn top 52 and has an open center to receive the linking tube 40. The linking tube 40 includes an open diameter large enough to allow the external tubing 32 to be inserted within the linking tube 40. The port stud 44 includes a threaded outside surface. Typically, the port stud 44 has a larger diameter top section 58 and smaller diameter bottom section 60. The top section 58 of the port stud 44 includes a collar cavity 62 with an open entrance 64 from the top 66 of the port stud 44. The collar cavity 62 includes a slightly conical shaped bottom 68 to receive the linking tube ferrule 42. The bottom section 60 of the port stud 44 has a cylindrical cavity that provides a tube opening 70 between the bottom 72 of the collar cavity 62 and the bottom 74 of the bottom section 60 of the port stud 44. The tube opening 70 of the bottom section 60 of the port stud 44 is slightly larger than the outside diameter of the linking tube 40. The stud nut 46 includes an open top cavity 76 connected to a threaded bottom cavity 78. The open top cavity 76 of the stud nut 46 is large enough to receive the main body 50 of the tube cap 38. The bottom threaded cavity 78 of the stud nut 46 is threaded to receive the threaded bottom section 60 of the port stud 44. The stud nut 46 has an opening at the bottom 80 of the stud nut 46. The stud nut 46 acts as a turning surface to be gripped by the user. The port ferrule 48 is slightly larger then the opening to the bottom threaded cavity 78 of the stud nut 46 at the bottom 80 of the stud nut 46. The port ferrule 48 has an open center 82 to receive the linking tube 40.

The external tubing 32 passes through the opening 54 in turn top 52 of the tube cap 38. The external tubing 32 is then inserted into the top end 84 of the linking tube 40 and is secured to the linking tube 40. The external tubing 32 can be secured to the linking tube 40 by thermal bonding, chemical adhesive, brazing, welding or other metallurgical attachment, depending on the materials used for the external tubing 32 and linking tube 40. Typical materials used for the external tubing 32 are a stainless steel and polymerics, such as polyether ether ketone. In all cases of attachment of the external tubing 32 to the linking tube 40, the desire place of attachment is at the bottom end 86 of the linking tube 40. The external tubing 32 is inserted along the length of the linking tube 40 such that there is coplanarity between the end 36 of the external tubing 32 and the bottom end 86 of the linking tube 40. Attachment at the end 36 of the external tubing 32 and the bottom end 86 of the linking tube 40 also provides a seal between the external tubing 32 and the linking tube 40. The external tubing 32 and the linking tube 40 can also be attached at the top end 82 of the linking tube 40. The purpose of securing the external tubing 32 to the linking tube 40 is to prevent movement of the external tubing 32 in relation to the bottom end 86 of the linking tube 40. If the external tubing 32 and the linking tube 40 are attached other than at the bottom end 86 of the linking tube 40, the space between the outside diameter of the external tubing 32 and the inside diameter of the linking tube 40 should still be sealed. The end 36 of the external tubing 32 and the bottom end 86 of the linking tube 40 can be optionally coated with or made of a malleable metal or other material capable of being compressed. Whereby, the malleable material upon compression against the shoulder 24 of the bottom 22 of the bottom section 18 of the port 10 deforms under force of compression to fill and seal slight voids which may exist between the bottom end 86 of the linking tube 40 and the shoulder 24 at the bottom 22 of the bottom section 18 of the port 10.

The linking tube ferrule 42 is positioned about the linking tube 40 near the top end 82 of the linking tube 40, prior to installation of the linking tube 40. There is a tight fit between the linking tube ferrule 42 and the linking tube 44. The fit is tight enough so that the linking tube ferrule 42 does not slide along the linking tube 40 during normal use, but not too tight such that the linking tube ferrule 42 is slidable along the linking tube 40 if enough pressure is applied. The linking tube ferrule 42 is in effect a collar or anything else that can be tightly fitted to the linking tube 40 and therefore does not have to be a ferrule. The linking tube 40 with the external tubing 32 attached is inserted into open entrance 64 at the top 66 of the port stud 44 and on through the collar cavity 62 of the top section 58 of the port stud 44. The linking tube 40 with the external tubing 32 attached is further inserted into the tube opening 70 of the bottom section 60, so it extends beyond the bottom section 60 of the port stud 44.

The tube cap 38 threads onto the threaded top section 58 of the port stud 44. The stud nut 46 threads onto the threaded bottom section 60 of the port stud 44, such that a portion of the threaded bottom section 60 of the port stud 44 protrudes beyond the stud nut 46. A thread locking compound is used between the threads of bottom threaded cavity 78 of the stud nut 46 and the threads of bottom section 60 of the port stud 44. Whereby, the coupling device 30 is threaded into the port 10 by inserting the exposed bottom section 60 of the port stud 44 into the threaded cavity of the port 10 and turning. The coupling device 30 is turned by turning the stud nut 46 to tighten the coupling device 30 in the port 10. The thread locking compound in effect glues the port stud 44 and the stud nut 46 together, so that the act of turning the stud nut 46 turns the port stud 44 into the port 10. Over tightening the coupling device 30 in the port 10 by applying too much torque to the stud nut 46 can cause damage to the port 10 and the coupling device 30. Thread locking compounds have different holding strengths. So a thread locking compound is chosen that allows the stud nut 46 to break free of the port stud 44, if the coupling device 30 is being over tightened in the port 10 when turning the stud nut 46. This allows for a controlled failure in the event excessive force is applied to the stud nut 46.

The port ferrule 48 receives the bottom end 86 of the linking tube 40 with the external tubing 32 attached, such that the bottom end 86 of the linking tube 40 extends beyond the port ferrule 78. The length of linking tube 40 which extends beyond the port ferrule 78 is controlled by the tube cap 38. The more the tube cap 38 is threaded onto the port stud 44, the more the linking tube 40 extends beyond the port ferrule 78. This is due to the linking tube ferrule 42 being tight enough about the linking tube 40 and being pushed by the tube cap 38. When the linking tube ferrule 42 bottoms out in the collar cavity 62 of the port stud 44, the linking tube 40 will not be inserted any further. When the linking tube 40 bottoms out in the port 10, the linking tube 40 will not be compressed any further because the linking tube ferrule 42 will break free and slide down the linking tube 40 due to the any excessive pressure applied that meets the design threshold for the linking tube ferrule 42 to break free.

Figure 4:
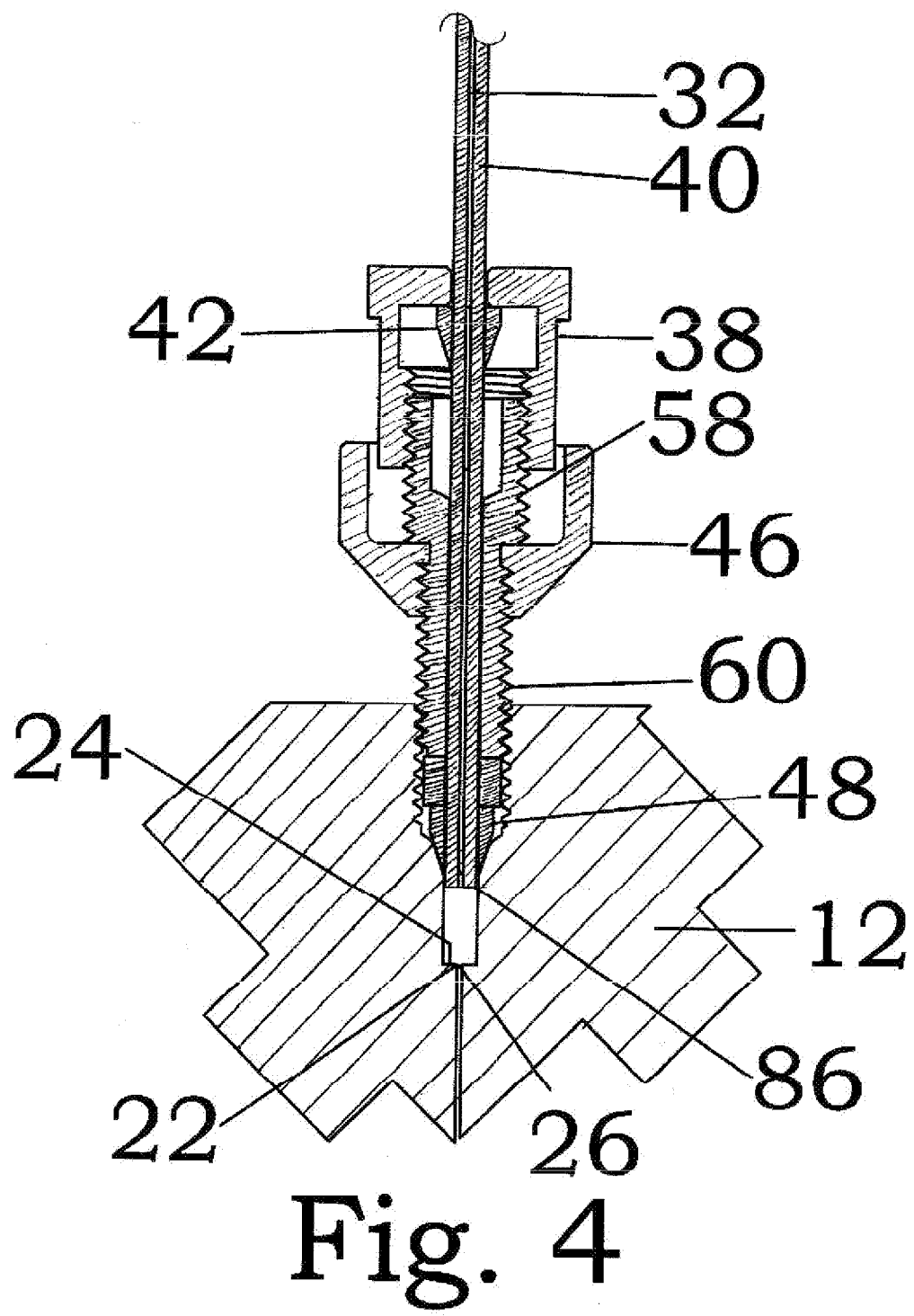
FIG. 4 is a cutaway view of a coupling device during installation in a port according to the present invention.
Figure 5:
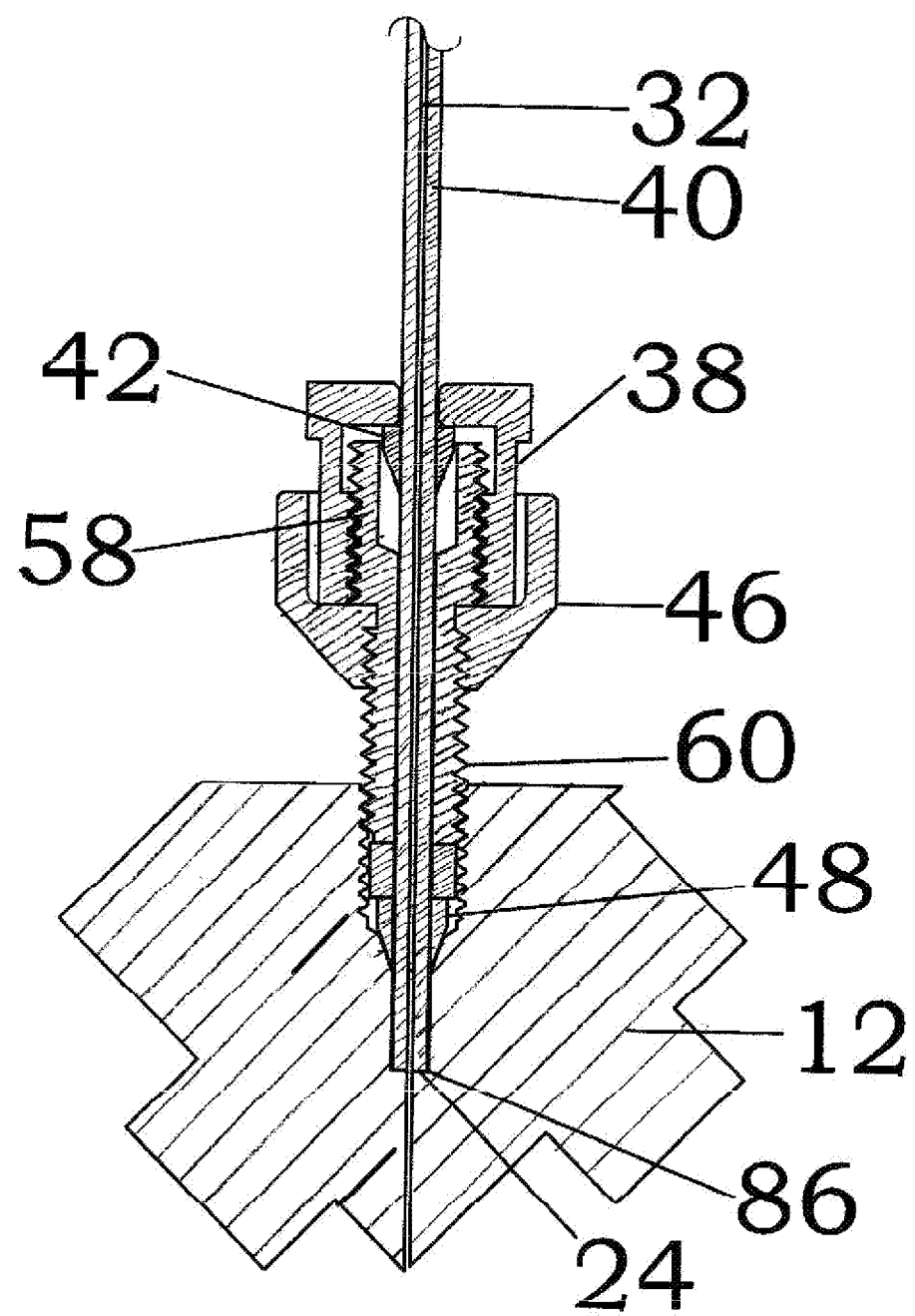
FIG. 5 is a cutaway view of a coupling device during installation in a port according to the present invention.

One method to install the coupling device 30 is to thread the tube cap 38 using the turn top 52 so that it threads on the port stud 44 such that the linking tube 40 protrudes minimally, but distinctly beyond the tip 88 of port ferrule 78, as shown in FIG. 4. The coupling device 30 is then guided into the port 10 and hand tightened into the port 10 using the stud nut 46. The port stud 44 is hand tighten to a state which compresses the port ferrule 78 adequately to hold the linking tube 40 against longitudinal slippage in the port ferrule 78, as shown in FIG. 4. But, not to compress the port ferrule 78 so tight as to preclude further adjustment of linking tube 40 downward into the port 10 by turning the tube cap 38. Next, tighten the tube cap 38 until a secure stop of the linking tube 40 against the shoulder 24 of the bottom 22 of the bottom section 18 of the port 10 is detected by a sudden increase in resistance to further tightening of the tube cap 38, as shown in FIG. 5. At this time it is recommended to reverse the direction of tightening tube cap 38, so as to loosen it very slightly. Then, apply a final tightening torque to the stud nut 46 so as to exert both longitudinal and radial compressive forces through the port ferrule 78 to the linking tube 40, forming a seal between the inner diameter of the port ferrule 78, and the outer diameter of the linking tube 40. Finally, apply a final tightening of the tube cap 38 to press the bottom end 86 of the linking tube 40 against the shoulder 24 of the port 10.

If using a malleable material at the bottom end 86 of the linking tube 40, one would not back off the tube cap 38 prior to applying final tightening of the stud nut 46 and the tube cap 38 is used to apply final tightening torque. Thus, converting rotational force about the tube cap 38 to longitudinal force, applied through linking tube ferrule 42 to linking tube 40, to ultimately deform the malleable metal coating or other deformable sealing material between the linking tube 40 and shoulder 24 of the port 10. This method of tightening can reduce the potential for chemical residuals to become entrapped in miniscule dead volumes which are associated with the perimeter of the cylindrical volume below the cone-shaped port ferrule 78. In this method of use, the port ferrule 78 is not required to provide sealing surfaces between the port ferrule 78 and the linking tube 40. Rather, the port ferrule 78 provides mechanical stabilization of linking tube 40 to hold the linking tube 40 concentric with the opening at the bottom section 18 of the port 10.

The linking tube ferrule 42 may be permanently fixed to the linking tube 40. The linking tube ferrule 42 being permanently fixed would allow maximum longitudinal pressure to be applied at the bottom end 86 of the linking tube 40 by turning tube cap 38, thereby allowing maximum tip sealing pressure of the bottom end 86 against the shoulder 24 of the port 10. But this allows for the unwanted side effect of allowing so much force to be applied as to bend or deform the linking tube 40. A crimped linking tube ferrule 42 may be employed to provide a maximum limit of force which may be applied before the linking tube ferrule 42 begins to slide along the linking tube 40. In this fashion, a safety precaution against damage is implemented. Additionally, sighting lines (not shown) can be scribed on the outside of the main body 50 of the tube cap 38 to indicate the relative depth of insertion of the linking tube 40 into the port stud 44 or the port 10. These sighting lines might be scribed in such a way provide a measuring index for parasitic dead volumes. Also, the external tubing 32 can be replaced by a single tubing which acts also as the linking tube 40. Whereby, the linking tube ferrule 42 would have to be installed after the single tubing is inserted into the tube cap 38.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

I claim:

1. A method of coupling a narrow diameter tubing having an end, to a CPI port of a device, the CPI port having an entrance opening and having a bottom located distal from the the entrance opening and the CPI port further including a bottom opening that is proximal to the bottom and distal from the entrance opening of the CPI port, the bottom opening providing communication between the CPI port and a device opening in the device to which the CPI port is attached, comprising:

providing a coupling device which receives and retains the end of the narrow diameter tubing;

providing the coupling device such that it is adapted to mount to the CPI port;

providing the coupling device such that the coupling device is configured to be mechanically manipulated in order to move the end of the narrow diameter tubing with pressure against a shoulder of the port;

wherein the shoulder of the port is located at the bottom of the CPI port and surrounds the bottom opening of the CPI port;

providing a malleable material on the end of the narrow diameter tubing that will compress under force and provide a seal between the narrow diameter tubing and the CPI port;

inserting the narrow diameter tubing into the coupling device;

installing the malleable material on the bottom end of the narrow diameter tubing that will compress under force and provide a seal between the narrow diameter tubing and the shoulder that surrounds the bottom opening of the CPI port;

installing the coupling device into the entrance opening of the CPI port and mechanically manipulating the coupling device such that the coupling device moves the end of the narrow diameter tubing in order to force the end of the narrow diameter tubing against the shoulder of the CPI port; and the movement of the end of the narrow diameter tubing compressing the malleable material on the end of the narrow diameter tubing and forming a seal between the end of the narrow diameter tubing and the shoulder of the CPI port.

2. A method of coupling narrow diameter tubing, having an end, to a CPI port of a device, the CPI port having an entrance opening and having a bottom located distal from the the entrance opening and the CPI port further including a bottom opening that is proximal to the bottom and distal from the entrance opening of the CPI port, the bottom opening providing communication between the CPI port and a device opening in the device to which the CPI port is attached, comprising:

providing a coupling device that it is adapted to mount to the CPI port;

inserting a tube into the coupling device;

wherein the tube has a top end and a bottom end;

inserting the narrow diameter tubing into that tube at the top end of the tube;

wherein the tube retains the end of the narrow diameter tubing;

mechanically manipulating the coupling device such that the coupling device moves the end of the tube, with pressure against a shoulder of the port;

wherein the shoulder of the port is located at the bottom of the CPI port and surrounds the bottom opening of the CPI port;

attaching a malleable material around the end of the narrow diameter tubing and onto the end of the tube; and wherein the malleable material is located between the end of the narrow diameter tubing and the shoulder of the CPI port;

wherein the malleable material compresses under force when the coupling device is mechanically manipulated and provides a seal between the narrow diameter tubing and the CPI port.

3. The method of claim 2, further including attaching the narrow diameter tubing to the tube such that the narrow diameter tubing is fixed within the tube and moves with the tube.

4. The method of claim 2, further including installing the narrow diameter tubing within the tube such that the tube is moveable along the narrow diameter tubing.

5. The method of claim 4, further including moving the tube along the narrow diameter tubing to compress the malleable material.

\* \* \* \* \*